United States Patent [19]

Yamada et al.

[11] Patent Number: 4,935,119
[45] Date of Patent: Jun. 19, 1990

[54] AIR/FUEL RATIO SENSOR

[75] Inventors: Tetsusyo Yamada; Nobuhiro Hayakawa, both of Aichi, Japan

[73] Assignee: NGK Spark Plug Co., Ltd., Nagoya, Japan

[21] Appl. No.: 832,798

[22] Filed: Feb. 25, 1986

[30] Foreign Application Priority Data

Feb. 25, 1985 [JP] Japan ................... 60-36029

[51] Int. Cl.$^5$ ............................................ G01N 27/46
[52] U.S. Cl. ..................... 204/425; 204/412; 204/426; 204/429
[58] Field of Search ............. 204/15, 412, 421–429

[56] References Cited

U.S. PATENT DOCUMENTS

| 3,791,936 | 2/1974 | Pebler et al. | 204/427 |
|---|---|---|---|
| 4,225,559 | 9/1980 | Achari et al. | 204/424 |
| 4,304,652 | 12/1981 | Chiba et al. | 204/426 |
| 4,322,383 | 3/1982 | Yashda et al. | 422/98 |
| 4,416,763 | 11/1983 | Fujishiro . | |
| 4,498,968 | 2/1985 | Yamada et al. | 204/426 |
| 4,502,939 | 3/1985 | Holfelder et al. | 204/426 |
| 4,505,803 | 3/1985 | Mase et al. . | |
| 4,578,172 | 3/1986 | Yamada et al. | 204/425 |

FOREIGN PATENT DOCUMENTS 200844 12/1982 Japan .
148946 9/1983 Japan .
190646 10/1984 Japan .

Primary Examiner—T. Tung
Attorney, Agent, or Firm—Sughrue, Mion, Zinn, Macpeak and Seas

[57] ABSTRACT

An air/fuel ratio sensor is described, comprising an oxygen pump element composed of a solid electrolyte having a pair of electrodes on opposite sides thereof, a gas diffusing section section that is in contact with one electrode on said oxygen pump element and which accepts a limited inflow of a gas to be analyzed, and an oxygen gas detecting element that is based on a transition metal oxide disposed within said gas diffusing section, the resistance of which varies in proportion to the partial pressure of oxygen gas in the gas to be analyzed.

5 Claims, 5 Drawing Sheets

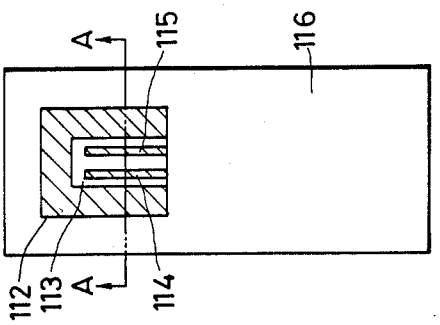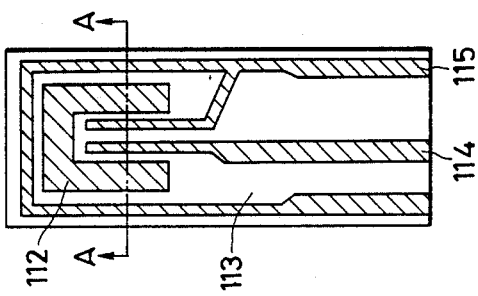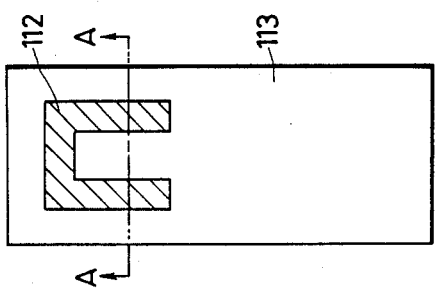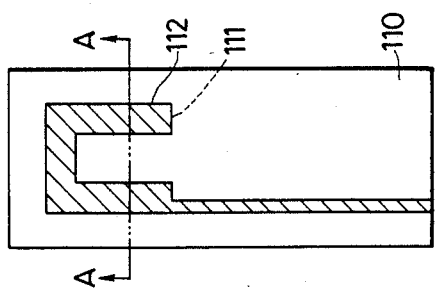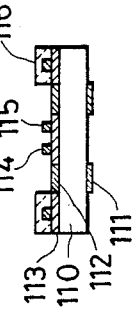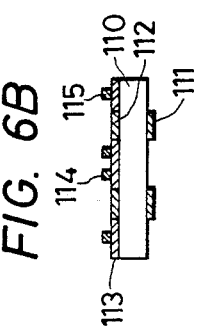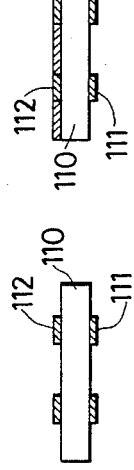

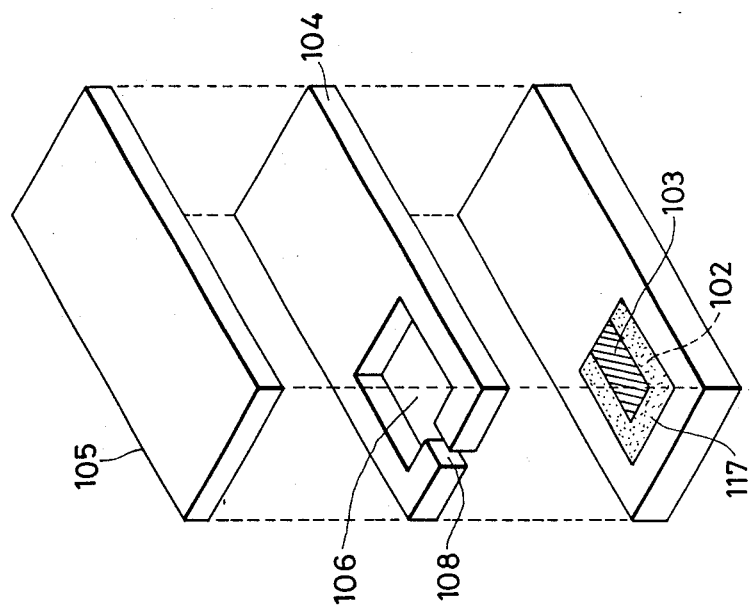
FIG. 10
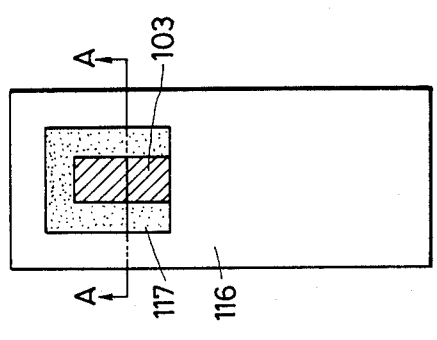
FIG. 8A
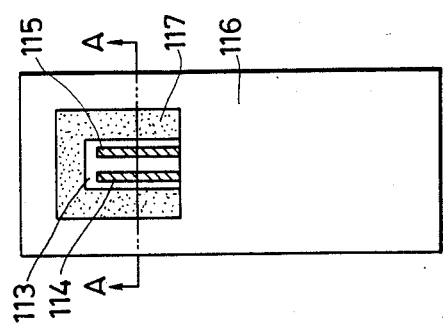
FIG. 9A
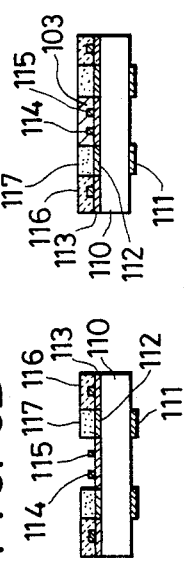
FIG. 8B
FIG. 9B

AIR/FUEL RATIO SENSOR

BACKGROUND OF THE INVENTION

The present invention relates to an air/fuel (A/F) ratio sensor for detecting the A/F ratio of an air/fuel mixture being supplied into a combustor. More particularly, the present invention relates to an A/F ratio sensor that is capable of detecting the A/F ratio of an air/fuel mixture using an oxygen ion conductive solid electrolyte over the full operating range, including the lean region (where air is in excess of the stoichiometric value) to the rich region (where fuel is in excess of the stoichiometric value).

With a view to improving fuel economy and reducing emissions, some conventional combustors such as internal combustion engines are provided with the capability of feedback control, involving the detection of oxygen levels in the exhaust gas and control of the air/fuel mixture in the combustion chamber so as to burn it at an A/F ratio in the vicinity of the stoichiometric value. An A/F ratio sensor commonly used to detect the concentration of oxygen in the exhaust gas takes the form of an oxygen sensor that is based on a transition metal oxide such as $TiO_2$ or $CoO$, the resistance of which varies depending upon the partial pressure of oxygen gas in the gas to be analyzed. Generally, this type of A/F ratio sensor produces an output voltage that changes abruptly at the stoichiometric value of the A/F ratio of the air/fuel mixture.

Attempts are constantly being made to maximize the performance of combustors, in addition to providing fuel economy improvements and emissions reduction, by means of performing feedback control to attain a desired A/F ratio that is adaptive to a specific state of operation of the combustor. This goal, however, is not attainable by the aforementioned oxygen sensor which is merely capable of detecting the stoichiometric value of the A/F ratio of the air/fuel mixture.

SUMMARY OF THE INVENTION

In order to solve the aforementioned problem, the present invention provides a novel A/F ratio sensor comprising an oxygen pump element composed of a solid electrolyte having a pair of electrodes on opposite sides, a gas diffusing section that is in contact with one electrode on said oxygen pump element and which accepts a limited inflow of a gas to be analyzed, and an oxygen gas detecting element that is based on a transition metal oxide disposed within said gas diffusing section, the resistance of which varies in proportion to the partial pressure of oxygen gas in the gas to be analyzed.

BRIEF DESCRIPTION OF THE DRAWINGS

FIGS. 4 to 9 show a sequence of steps for fabricating the sensor of FIG. 3, wherein A of each figure is a plane view and B is a cross section taken on line A-A;

FIG. 10 shows the sensor of FIG. 3 in an unassembled form;

DESCRIPTION OF THE PREFERRED EMBODIMENTS

A typical example of the material of the solid electrolyte is a solid solution of zirconia and yttria or calcia. Other usable materials include solid solutions of cerium dioxide, thorium dioxide, and hafnium dioxide, a solid solution of the perovskite type oxide, and a solid solution of a trivalent metal oxide.

The electrodes on the solid electrolyte may be formed from platinum or gold by various methods; in one method, a paste based on a powder of platinum, gold or any other appropriate metal is printed in a predetermined pattern on the solid electrolyte by a thick-film deposition technique, followed by sintering of the printed coat; in another method, the powder of the starting material is applied onto the solid electrolyte by a suitable thin-film deposition technique such as flame spraying, chemical plating, or evaporation.

The transition metal oxide which is used as the principal component of the oxygen gas detecting element is an oxide of an element selected from those having atomic numbers of 21 (Sc) to 30 (Zn), 39 (Y) to 48 (Cd), 57 (La) to 80 (Hg), and 89 (Ac) to 103 (Lr). Oxides of these elements have a tendency to form non-stoichiometric compounds wherein the ratio of a specific metal element to oxygen assumes a non-integral number. Because of this non-stoichiometricity, the oxides of the elements listed above will experience great changes in electrical conductivity depending upon the oxygen partial pressure in the gas to be analyzed. This effect is the same whether the oxides listed above are employed individually or in combination. Preferred examples are $TiO_2$, $CoO$, $SnO_2$, $ZnO$, $Nb_2O_5$, and $Cr_2O_3$, primarily because they show noticeable changes in electrical conductivity in response to variations in the oxygen partial pressure, and, in addition, these oxides have superior durability. They may be rendered even more durable by mixing a transition metal oxide, say, $CoO$, with an oxide of a non-transition metal such as $MgO$.

Referring to the partial fragmentary views shown in FIG. 1A to 1E, several layouts of the three essential components, i.e., the oxygen pump element 2 disposed on the solid electrolyte 1, the oxygen gas detecting element 3, and the gas diffusing section 4, are described below.

Figure 1A:
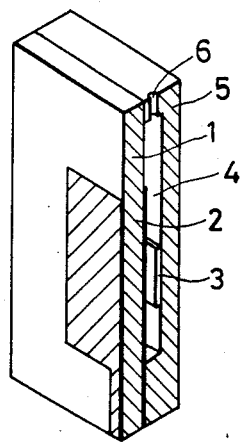
FIGS. 1A to 1E are partial fragmentary perspective views illustrating four different variations of the basic structure of the A/F ratio sensor of the present invention.

In the embodiment of FIG. 1A, the oxygen pump element 2 and the oxygen detecting element 3 are disposed in a face-to-face relationship with a small gap provided therebetween. The small gap forms a gas diffusing section 4 that accepts a limited inflow of the gas to be analyzed through a tiny aperture 6. The oxygen gas detecting element 3 disposed on a shield plate 5 is connected to an electrode and conductive lead (not shown).

Figure 1B:
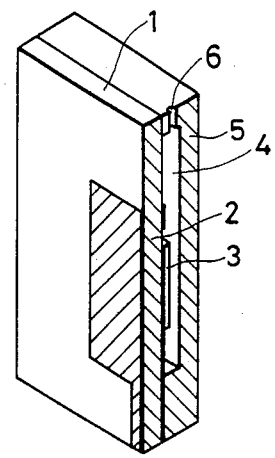

The embodiment shown in FIG. 1B differs from that of FIG. 1A in that the oxygen gas detecting element 3 is disposed on the solid electrolyte 1. If, as in the case of FIG. 1B, both the oxygen pump element 2 and the oxygen gas detecting element 3 are provided on the same solid electrolyte plate 1, the detecting element 3 may be partly surrounded by the electrode disposed on the side of the pump element 2 where the element 3 is formed; alternatively, the detecting element 3 may be formed in such a manner that it overlies the pump element 2.

Figure 1C:
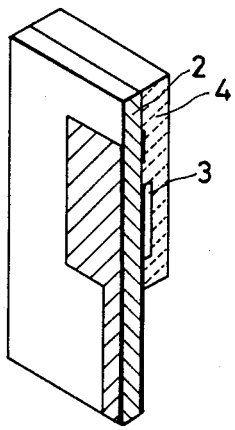

The design shown in FIG. 1C is the same as that of FIG. 1B in that the oxygen gas detecting element 3 and the oxygen pump element 2 are disposed on the same solid electrolyte plate 1. The difference is that a porous member is employed as the gas diffusing means; that part of the porous member which is in the neighborhood of the electrode provided on the side of the oxygen pump element which faces the porous member serves as the gas diffusing section 4.

Figure 1D:
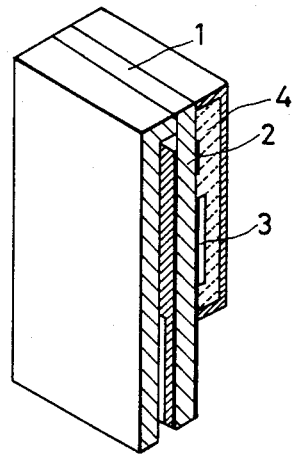

The configuration shown in FIG. 1D is the same as that of FIG. 1C in that the oxygen pump element 2 and the oxygen gas detecting element 3 are disposed on the same solid electrolyte plate 1 and are covered with a porous member. The difference is that this porous member is composed of a surface layer having a low porosity and an inner layer having a high porosity, the latter providing the gas diffusing section 4. In the embodiment shown, the electrode on the side of the pump element 2 which is not in contact with the gas diffusing section 4 makes contact with the atmospheric air by way of an air introducing channel that may be provided by any known method.

Figure 1E:
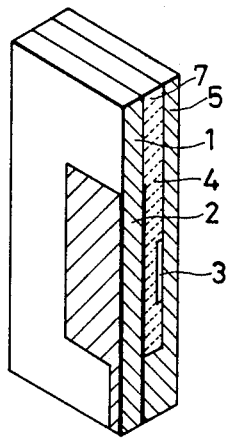

A sensor shown in FIG. 1E is different from that shown in FIG. 1A in that the gas diffusing section is made of a porous material 7. In FIG. 1E, the oxygen pump element 2, the gas diffusing section made of the porous material 7 and the shield plate 5 are laminated one on another without any internal space (FIG. 1A). For this reason, the shape holding characteristic may be ensured during the manufacture processes. Also, the porosity of the porous material 7 may readily be controlled in comparison with the control of the diameter of the aperture 6 to thereby provide A/F ratio sensors having a uniform property.

The components shown in FIG. 1A to 1E may be combined as may be required for a particular purpose; for example, the sensor design of FIG. 1A may be provided with an air introducing channel as in the embodiment of FIG. 1D.

The shield plate 5 may be made of $Al_2O_3$, mullite, spinel, or the like, and the porous member 4 may also be formed of $Al_2O_3$, mullite, spinel or the like. In order to ensure a uniform distribution in terms of the concentration of the gas to be analyzed within the small gap, particularly the one existing between components, the porous member 4 should have a thickness of from 0.01 to 0.2 mm. The degree by which the porous member 4 limits the diffusion of a gas to be analyzed may be adjusted by controlling the porosity of the member 4, which may, in turn, be adjusted by controlling the particle size or the refractory nature of the powder of the starting material. If the porous member 4 is used as gas diffusing section, it preferably has an apparent porosity of at least 5% in order to ensure a uniform distribution of the gas to be analyzed.

The operation of the A/F ratio sensor of the present invention is hereunder described.

When the air/fuel mixture is in the lean region, the sensor is put into the exhaust gas and the electrode on the outer side of the oxygen pump element (the side not in contact with the gas diffusion section) is supplied with a positive voltage while a negative voltage is applied to the electrode on the side of the pump element that is in contact with the gas diffusing section. As a result, oxygen ions migrate through the solid electrolyte of the oxygen pump element from the electrode 2 facing the gas diffusing section toward the outer electrode, whereby the oxygen gas in the gas diffusing section is pumped out of the oxygen pump element.

As the oxygen gas is pumped out of the gas diffusion section in the manner described above, a difference is produced between the partial pressure of oxygen gas within the gas diffusing section and that of oxygen in the gas to be analyzed, because of the action of the gas diffusion limiting means provided at the gas diffusing section. This differential oxygen partial pressure is measured in terms of the resistance of the oxygen gas detecting element. If the amount of current (pumping current) flowing through the oxygen pump element is adjusted such that the measured value of resistance will be maintained at a predetermined level, a substantially linear relationship is obtained between the pumping current which is proportional to the differential oxygen partial pressure and the content of oxygen in the gas to be analyzed, thereby enabling the determination of the oxygen level of that gas.

When the air/fuel mixture is in the rich region, the oxygen partial pressure is held low even if the oxygen pump element is not actuated to reduce the partial pressure of oxygen in the gas diffusing section. Therefore, in order to maintain the resistance of the oxygen gas detecting element at a constant value, the direction of the pumping current flowing through the pump element should be reversed. To state it more specifically, the oxygen in the gas diffusing section is consumed by the unburnt hydrocarbons and carbon monoxide in the exhaust gas, and the partial pressure of oxygen in the gas diffusing section becomes so low as to produce a resistance that is higher than a predetermined value. Therefore, in order to maintain the resistance at the predetermined value, oxygen must be pumped into the gas diffusing section by operating the oxygen pump element. To this end, the pumping current is caused to flow in the direction opposite to that used when the air/fuel mixture is in the lean region. In addition, the amount of the required pumping current is proportional to the amounts of the unburnt hydrocarbons and carbon monoxide in the exhaust gas.

However, if, as in the embodiment shown in FIG. 1A to 1C and 1E, the electrode on that side of the oxygen pump element which is not in contact with the gas diffusing section is exposed to the atmosphere being analyzed, not much oxygen is available for the oxygen pump element in the rich region, and the linear relationship between the pump current and A/F ratio ceases if the A/F ratio becomes lower than about 13. In order to solve this problem, a sufficient amount of oxygen to be utilized by the oxygen pump element must be supplied by introducing the atmospheric air into the area around the electrode on the side of the pump element which is not in contact with the gas diffusing section, as shown in FIG. 1D.

Figure 2:
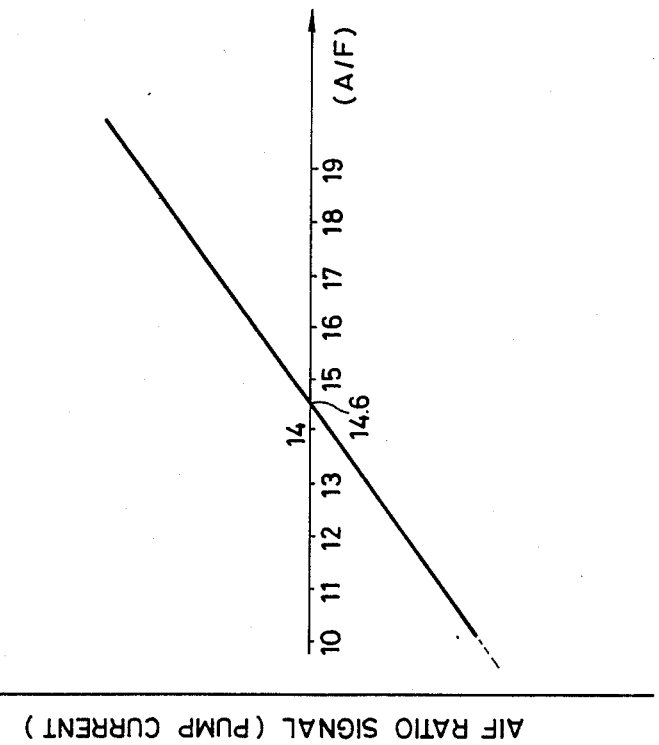
FIG. 2 is a graph showing the operating characteristics of the sensor of the present invention.

To summarize the foregoing explanation, if the pumping current that is caused to flow through the oxygen pump element of the A/F ratio sensor of the present invention is adjusted so that the output from the oxygen detecting element will be maintained at a predetermined level, the resulting pump current will be proportional to the A/F ratio of the air/fuel mixture being analyzed. This linear relationship is shown in FIG. 2, wherein the dashed line refers to the range of A/F ratio that can be measured when the atmospheric air is used as a source of oxygen to be utilized by the oxygen pump element.

It should be mentioned that in accordance with the present invention the A/F ratio determination can be also accomplished by measuring the resistance of the oxygen detecting element that develops when the pumping current is maintained at a control level.

Figure 3:
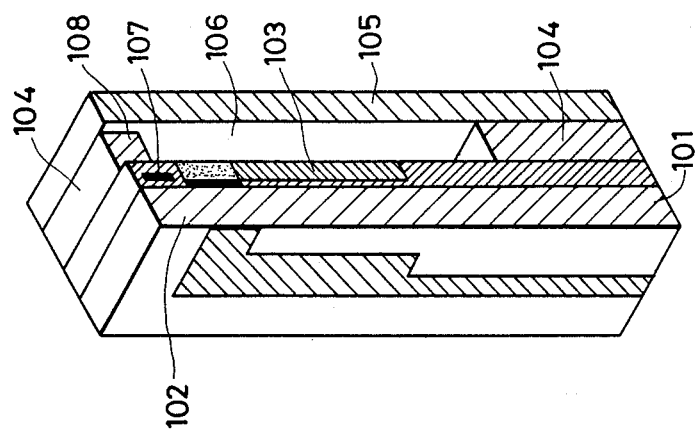
FIG. 3 is a partial fragmentary perspective view of the sensor in accordance with a first embodiment of the present invention.

A first embodiment of the A/F ratio sensor of the present invention is hereunder described with reference to FIG. 3, which is a partial fragmentary perspective view of the sensor.

The sensor of this embodiment comprises a solid electrolyte plate 101 on which both an oxygen pump element 102 and an oxygen gas detecting element 103 are disposed, with a gas diffusing section 106 being in the form of a small gap that is defined by the solid electrolyte plate 101, a spacer 104 and a shield plate 105. The spacer 104 is provided with a gas diffusion limiting aperture 108. A heating element 107 is provided on the solid electrolyte plate 101 in an area close to the oxygen pump element 102.

The sensor of the first embodiment may be fabricated by the procedures whose sequence is illustrated in FIGS. 4 to 9; (A) of each figure is a plan view of the components being assembled, and (B) is a cross section taken on line A-A.

First, as shown in FIG. 4, a green sheet 110 measuring 5×30×0.6 mm that is made of a solid solution of $Y_2O_3$ and $ZrO_2$ and which corresponds to the solid electrolyte plate 101 is prepared. Then, electrode patterns 111 and 112 for the oxygen pump element 102 are formed on opposite sides of the sheet 110 by applying a platinum paste by a thick-film process.

In the next step, a green $Al_2O_3$ sheet 113 with a window and having a thickness of 0.1 mm is placed on the side of the electrode pattern 112 that is exposed in the window as shown in FIG. 5, and the two sheets are pressed together to form a unitary assembly.

Subsequently, as shown in FIG. 6, electrode patterns 114 and 115 serving as the electrode for the oxygen gas detecting element 103 and the heating element 107 are formed on the sheet 113 by applying a platinum paste by a thick-film process.

Then, as shown in FIG. 7, a green $Al_2O_3$ sheet 116 with a window and having a thickness of 0.1 mm is placed on the sheet 113 to cover its entire area except for the electrode pattern 112 and the area where the oxygen gas detecting element is to be disposed.

In the next step, the electrode 112 is covered with a protective layer 117 made of porous zirconia, and the layer is fired.

Subsequently, a $TiO_2$ paste is applied by a thick-film printing process to form a layer that covers the electrode patterns 114 and 115, and the layer is fired.

In a separate step, a green $Al_2O_3$ sheet 104 measuring 5×30×0.1 mm that is provided with the gas diffusing section 106 and the gas diffusion limiting aperture 108 and which will serve as a spacer is prepared. Also, a green $Al_2O_3$ sheet measuring 5×30×0.5 mm is placed and compressed onto a shield plate 105, which then is assembled with the spacer 104 into a unitary structure by firing in an inert atmosphere.

In the final step, the solid electrolyte plate 101 carrying the oxygen pump element 102 and the oxygen gas detecting element 103 is bonded to the shield plate 105 and the spacer by a glass adhesive, thereby producing an A/F ratio sensor.

The operating range of the thus fabricated A/F ratio sensor is such that it is unable to sense the values of A/F ratio in the rich region if A/F becomes lower than about 13. However, with ordinary automotive gasoline engines, the A/F ratio will not become lower than 13 even if the driver depresses the accelerator pedal to its fullest extent such as in the case of sudden acceleration. This means the A/F ratio sensor in accordance with the first embodiment can be used over the practically full operating range for controlling the A/F ratio of an air/fuel mixture being supplied into automotive engines.

Figure 12:
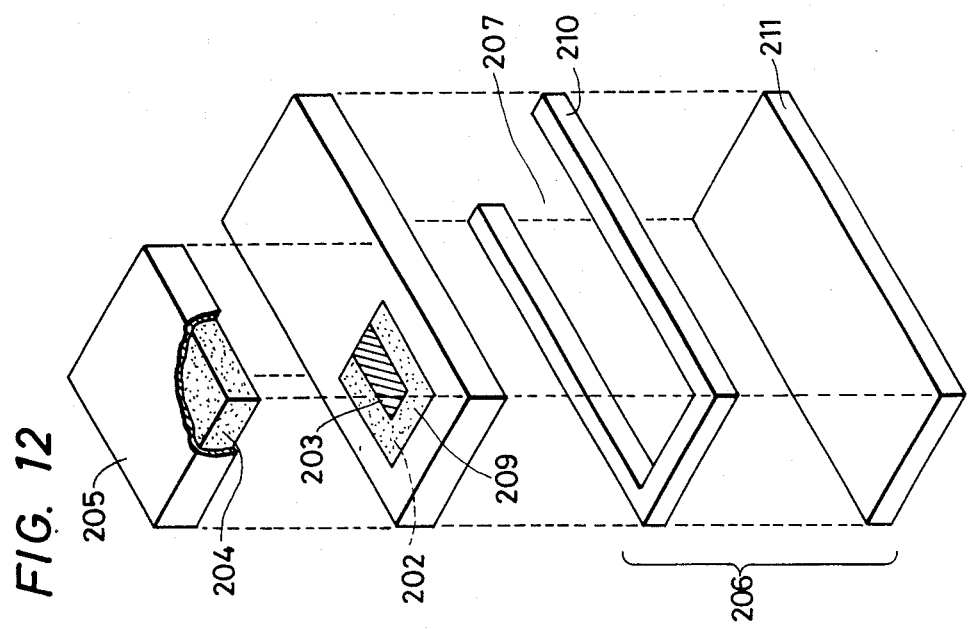
FIG. 12 shows the sensor of FIG. 11 in an unassembled form.
Figure 11:
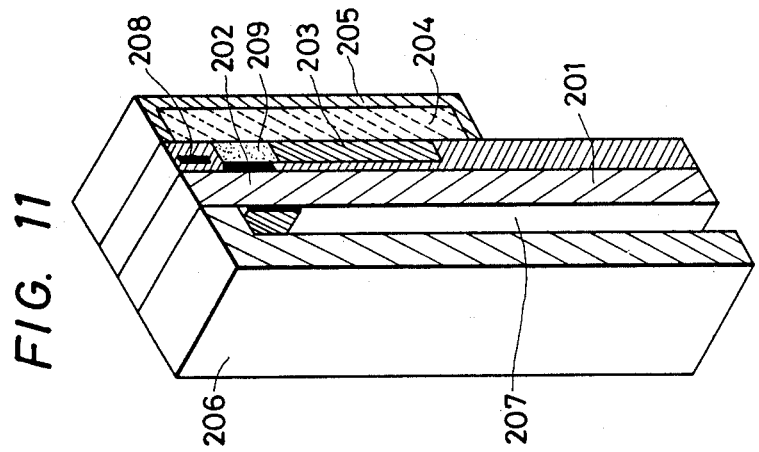
FIG. 11 is a partial fragmentary perspective view of the sensor in accordance with a second embodiment of the present invention.

A second embodiment of the A/F ratio sensor of the present invention is hereunder described with reference to FIG. 11 which shows a partial fragmentary perspective view of the sensor and to FIG. 12 which shows the sensor in an unassembled form.

The sensor of this embodiment comprises a solid electrolyte plate 201 on which both an oxygen pump element 202 and an oxygen gas detecting element 203 are disposed, with a gas diffusing section in the form of a porous member A 204 with a high porosity, which is covered by a porous member B 205 with a lower porosity that serves as a gas diffusion limiting section. The area around the electrode formed on the side of the oxygen pump element 202 which is not in contact with the porous member A 204 is exposed to the atmospheric air that is introduced through an air introducing channel 207 provided by a channel former 206. A heating element 208 is disposed in the area close to the oxygen pump element 202.

The solid electrolyte plate is provided with the oxygen pump element 202 and the oxygen gas detecting element 203 by the same procedures as employed in the case of the first embodiment. Thereafter, as shown in FIG. 12, the porous member A 204 with a porosity of 3% that is made of $Al_2O_3$ particles at least 50% of which have a size of 5 microns or less is provided such that it covers an electrode protective layer 209 for the oxygen pump element 202 and the oxygen gas detecting element 203, and said porous member A 204 is covered with the porous member B 205 with a porosity of 1% that is made of $Al_2O_3$ particles at least 80% of which have a size of 2.5 microns or less. The porous member B 205 serves as a gas diffusion limiting section. The air introducing channel 207 is provided by the channel former 206 that is comprised of a stress relaxing layer 210 which is a sintered mixture of $ZrO_2$ and $AlO_3$ and a support 211 made of $Al_2O_3$.

The sensor of the present invention allows the A/F ratio of an air/fuel mixture supplied into an internal combustion engine to be controlled over the full operating range including the lean and rich regions. Additionally, the configuration of the sensor is simplified in that it does not have to use a reference oxygen source for the purpose of measuring the oxygen level of the exhaust gas. In the absence of a reference oxygen source, the sensor will perform reliably without improper measurement that would result from variations in the partial pressure of oxygen gas in a reference oxygen source, if such were used.

A particular advantage of the sensor of the present invention is its good response characteristics that originate from the use of a transition metal oxide as the material of the oxygen gas detecting element.

We claim:

1. An air/fuel ratio sensor comprising an oxygen pump element composed of a solid electrolyte having a pair of electrodes on opposite sides thereof, a gas diffusing section that is in contact with one electrode on said oxygen pump element and which accepts a limited inflow of a gas to be analyzed, said gas diffusing section comprising a porous member having an inner layer portion of high porosity and a surface layer portion covering said inner layer portion and having a porosity lower than the porosity of said inner layer portion, said oxygen pump element being responsive to varying amounts of current pumped therethrough to affect a partial pressure of oxygen in said gas diffusing section, and an oxygen gas detecting element that is based on a transition metal oxide disposed within said gas diffusing section, said oxygen gas detecting element being responsive to a varying partial pressure of oxygen gas in said gas diffusion section to maintain a constant resistance value of said oxygen gas detecting element, wherein a relationship between an amount of current being pumped through said oxygen pump element and the partial pressure of oxygen gas in the gas to be analyzed is linear throughout a range bridging a stoichiometric air/fuel ratio.

2. An air/fuel ratio sensor according to claim 1 wherein said transition metal oxide is at least one member selected from the group consisting of $SnO_2$, $TiO_2$, $CoO$, $ZnO$, $Nb_2O_5$, and $Cr_2O_3$.

3. An air/fuel ratio sensor according to claim 1, wherein said inner layer portion of said porous member has a porosity of 3% made of $Al_2O_3$ particles at least 50% of which have a size of 5 microns or less and said surface layer portion of said porous member has a porosity of 1% made of $Al_2O_3$ particles at least 80% of which have a size of 2.5 microns or less.

4. An air/fuel ratio sensor according to claim 1, one of said pair of electrodes being disposed on a side of the oxygen pump element which is not in contact with the gas diffusing section, said sensor further comprising an air introducing section for introducing atmospheric air, said air introducing section contacting the electrode on the side of the oxygen pump element which is not in contact with the gas diffusing section, such that the electrode which is not in contact with the gas diffusing section is in contact with atmospheric air.

5. An air/fuel ratio sensor according to claim 1, wherein said porous member fills a small gap through which said gas to be analyzed diffuses.

* * * * *